United States Patent
Arless et al.

(10) Patent No.: US 7,951,140 B2
(45) Date of Patent: *May 31, 2011

(54) CATHETER WITH CRYOGENIC AND ELECTRICAL HEATING ABLATION

(75) Inventors: Steven G. Arless, Beaconsfield (CA);
Fredric L. Milder, Brookline, MA (US);
Marwan Abboud, Pierrefonds (CA);
Dan Wittenberger, L'lle Bizard (CA);
Sean Carroll, Rancho Cucamonga (CA)

(73) Assignee: Medtronic Cryocath LP, Toronto, Ontario (CA)

( * ) Notice: Subject to any disclaimer, the term of this patent is extended or adjusted under 35 U.S.C. 154(b) by 710 days.

This patent is subject to a terminal disclaimer.

(21) Appl. No.: 11/971,582

(22) Filed: Jan. 9, 2008

(65) Prior Publication Data
US 2008/0114345 A1  May 15, 2008

Related U.S. Application Data

(60) Division of application No. 11/219,061, filed on Sep. 2, 2005, now Pat. No. 7,465,300, which is a continuation of application No. 09/457,958, filed on Dec. 9, 1999, now Pat. No. 7,097,641.

(51) Int. Cl.
*A61B 18/02* (2006.01)

(52) U.S. Cl. .......................... 606/21; 606/33

(58) Field of Classification Search ............... 606/20–26
See application file for complete search history.

(56) References Cited

U.S. PATENT DOCUMENTS

| | | | |
|---|---|---|---|
| 3,439,680 A | 4/1969 | Thomas | |
| 3,507,283 A | 4/1970 | Thomas | |
| 3,823,575 A | 7/1974 | Parel | |
| 3,859,986 A | 1/1975 | Okada et al. | |
| 4,072,152 A | 2/1978 | Linehan | |
| 4,202,336 A | 5/1980 | van Gerven | |
| 4,206,609 A | 6/1980 | Durenec | |
| 4,278,090 A | 7/1981 | van Gerven | |
| 4,280,499 A | 7/1981 | Sguazzi | |
| 4,375,220 A | 3/1983 | Matvias | |
| 4,377,168 A | 3/1983 | Rzasa et al. | |
| 4,519,389 A | 5/1985 | Gudkin et al. | |
| 4,522,194 A | 6/1985 | Normann | |
| 4,641,649 A | 2/1987 | Walinsky et al. | |
| 4,860,744 A | 8/1989 | Johnson et al. | |
| 4,945,912 A | 8/1990 | Langberg | |
| 4,946,460 A | 8/1990 | Merry et al. | |
| 5,041,089 A | 8/1991 | Mueller et al. | |

(Continued)

FOREIGN PATENT DOCUMENTS

EP 0335022 A1 10/1989

(Continued)

*Primary Examiner* — Linda C Dvorak
*Assistant Examiner* — Amanda Scott
(74) *Attorney, Agent, or Firm* — Christopher & Weisberg, P.A.

(57) ABSTRACT

A catheter includes a cryoablation tip with an electrically-driven ablation assembly for heating tissue. The cryoablation tip may be implemented with a cooling chamber through which a controllably injected coolant circulates to lower the tip temperature, and having an RF electrode at its distal end. The RF electrode may be operated to warm cryogenically-cooled tissue, or the coolant may be controlled to conductively cool the tissue in coordination with an RF treatment regimen, allowing greater versatility of operation and enhancing the lesion size, speed or placement of multi-lesion treatment or single lesion re-treatment cycles.

19 Claims, 3 Drawing Sheets

U.S. PATENT DOCUMENTS

| | | |
|---|---|---|
| 5,139,496 A | 8/1992 | Hed |
| 5,147,355 A | 9/1992 | Friedman et al. |
| 5,188,602 A | 2/1993 | Nichols |
| 5,224,943 A | 7/1993 | Goddard |
| 5,275,595 A | 1/1994 | Dobak, III |
| 5,281,213 A * | 1/1994 | Milder et al. ............ 606/15 |
| 5,281,215 A | 1/1994 | Milder |
| 5,281,217 A | 1/1994 | Edwards et al. |
| 5,281,218 A | 1/1994 | Imran |
| 5,330,469 A | 7/1994 | Fleenor |
| 5,330,518 A | 7/1994 | Neilson et al. |
| 5,334,193 A | 8/1994 | Nardella |
| 5,342,357 A | 8/1994 | Nardella |
| 5,348,554 A | 9/1994 | Imran et al. |
| 5,383,876 A | 1/1995 | Nardella |
| 5,423,807 A | 6/1995 | Milder |
| 5,423,808 A | 6/1995 | Edwards et al. |
| 5,423,811 A | 6/1995 | Imran et al. |
| 5,425,375 A | 6/1995 | Chin et al. |
| 5,431,649 A | 7/1995 | Mulier et al. |
| 5,437,662 A | 8/1995 | Nardella |
| 5,514,129 A | 5/1996 | Smith |
| 5,520,684 A | 5/1996 | Imran |
| 5,529,067 A | 6/1996 | Larsen et al. |
| 5,531,677 A | 7/1996 | Lundquist et al. |
| 5,531,742 A | 7/1996 | Barken |
| 5,540,062 A | 7/1996 | Maytal |
| 5,540,655 A | 7/1996 | Edwards et al. |
| 5,545,161 A | 8/1996 | Imran |
| 5,562,720 A | 10/1996 | Stern et al. |
| 5,571,147 A | 11/1996 | Sluijter et al. |
| 5,603,221 A | 2/1997 | Maytal |
| 5,609,151 A | 3/1997 | Mulier et al. |
| 5,647,868 A | 7/1997 | Chinn |
| 5,647,871 A | 7/1997 | Levine et al. |
| 5,651,780 A | 7/1997 | Jackson et al. |
| 5,658,278 A | 8/1997 | Imran et al. |
| 5,674,218 A | 10/1997 | Rubinsky et al. |
| 5,680,860 A | 10/1997 | Imran |
| 5,697,927 A | 12/1997 | Imran et al. |
| 5,733,280 A | 3/1998 | Avitall |
| 5,733,281 A | 3/1998 | Nardella |
| 5,743,903 A | 4/1998 | Stern et al. |
| 5,755,715 A | 5/1998 | Stern et al. |
| 5,759,182 A | 6/1998 | Varney et al. |
| 5,800,488 A | 9/1998 | Crockett |
| 5,800,493 A | 9/1998 | Stevens et al. |
| 5,843,021 A | 12/1998 | Edwards et al. |
| 5,891,188 A | 4/1999 | Maytal |
| 5,893,885 A | 4/1999 | Webster, Jr. |
| 5,899,897 A | 5/1999 | Rabin et al. |
| 5,906,612 A | 5/1999 | Chinn |
| 5,906,614 A | 5/1999 | Stern et al. |
| 5,951,546 A | 9/1999 | Lorentzen |
| 5,957,961 A | 9/1999 | Maguire et al. |
| 5,967,976 A | 10/1999 | Larsen et al. |
| 6,015,407 A | 1/2000 | Rieb et al. |
| 6,019,783 A | 2/2000 | Philips et al. |
| 6,027,500 A | 2/2000 | Buckles et al. |
| 6,049,737 A | 4/2000 | Simpson et al. |
| 6,053,912 A | 4/2000 | Panescu et al. |
| 6,056,745 A | 5/2000 | Panescu et al. |
| 6,063,078 A | 5/2000 | Wittkampf |
| 6,106,518 A | 8/2000 | Wittenberger et al. |
| 6,119,041 A | 9/2000 | Pomeranz et al. |
| 6,123,702 A | 9/2000 | Swanson et al. |
| 6,165,174 A | 12/2000 | Jacobs et al. |
| 6,183,468 B1 | 2/2001 | Swanson et al. |
| 6,188,930 B1 | 2/2001 | Carson |
| 6,200,314 B1 | 3/2001 | Sherman |
| 6,206,876 B1 | 3/2001 | Levine et al. |
| 6,210,406 B1 | 4/2001 | Webster, Jr. |
| 6,217,573 B1 | 4/2001 | Webster |
| 6,235,019 B1 | 5/2001 | Lehmann et al. |
| 6,235,022 B1 | 5/2001 | Hallock et al. |
| 6,241,754 B1 | 6/2001 | Swanson et al. |
| 6,245,065 B1 | 6/2001 | Panescu et al. |
| 6,264,653 B1 | 7/2001 | Falwell |
| 6,273,886 B1 | 8/2001 | Edwards et al. |
| 6,283,960 B1 | 9/2001 | Ashley |
| 6,293,943 B1 | 9/2001 | Panescu et al. |
| 6,325,797 B1 | 12/2001 | Stewart et al. |
| 6,327,505 B1 | 12/2001 | Medhkour et al. |
| 6,378,525 B1 | 4/2002 | Beyar et al. |
| 6,379,348 B1 | 4/2002 | Onik |
| 6,451,011 B2 | 9/2002 | Tu |
| 6,471,697 B1 | 10/2002 | Lesh |
| 6,506,189 B1 | 1/2003 | Rittman, III et al. |
| 6,551,274 B2 | 4/2003 | Heiner |
| 6,602,227 B1 | 8/2003 | Cimino et al. |
| 6,648,879 B2 | 11/2003 | Joye et al. |
| 6,648,880 B2 | 11/2003 | Chauvet et al. |
| 6,682,501 B1 | 1/2004 | Nelson et al. |
| 6,796,980 B2 | 9/2004 | Hall |
| 6,858,025 B2 | 2/2005 | Maurice |

FOREIGN PATENT DOCUMENTS

| | | |
|---|---|---|
| EP | 0608609 A2 | 8/1994 |
| EP | 1378199 A1 | 1/2004 |
| EP | 1419742 A2 | 5/2004 |
| NL | 1004655 C | 6/1998 |
| WO | 9116859 A1 | 11/1991 |
| WO | 9605767 A1 | 2/1996 |
| WO | 9843547 A2 | 10/1998 |
| WO | 03096895 A1 | 11/2003 |
| WO | 2004045442 A1 | 6/2004 |

* cited by examiner

CATHETER WITH CRYOGENIC AND ELECTRICAL HEATING ABLATION

CROSS-REFERENCE TO RELATED APPLICATIONS

This application is a divisional of U.S. patent application Ser. No. 11/219,061, filed Sep. 2, 2005, which application is a continuation application of utility patent application Ser. No. 09/457,958, filed Dec. 9, 1999, by Steven G. Arless, et al., entitled CATHETER WITH CRYOGENIC AND HEATING ABLATION, now issued U.S. Pat. No. 7,097,641, the entirety of all of which are incorporated herein by reference.

STATEMENT REGARDING FEDERALLY SPONSORED RESEARCH

Not Applicable.

BACKGROUND OF THE INVENTION

The present application relates to cryocatheters and wands, i.e. to catheters and wands which are used to locally ablate tissue by extreme cooling contact. Such implements, henceforth generically referred to herein as "cryocatheters" or simply "catheters" may, for example, have an elongated body through which a cooling fluid circulates to a tip portion which is adapted to contact and freeze tissue. The invention also relates to cold-mapping catheters. In general, such catheters may be used to lower the temperature of tissue, such as cardiac wall tissue, to an extent such that signal generation or conduction ceases and allows one to map or confirm that the catheter is positioned at a particular lesion or arrhythmia conduction site. Cryocatheters, however, operate at lower temperatures, and are configured for ablation treatment, to cool the tissue to a level at which freezing destroys the viability of the tissue, and, in the case of cardiac tissue, permanently removes it as a signal generating or signal conducting locus. Such devices are also useful for tissue destruction in other contexts, such as the ablation of tumorous, diseased, precancerous or congenitally abnormal tissue. The invention also relates to electrically driven catheters, such as RF ablation catheters. These catheters have an arrangement of one or more electrodes at their tip configured to contact tissue and apply RF energy thereto so that the tissue heats up due to resistive heating, creating an ablation lesion that may extend to a depth of several millimeters or more. Such catheters have sometimes been equipped with coolant supplies in the prior art to cool the tip and prevent electrode charring, or to cool adjacent tissue and perform cold-mapping and ablation with the same instrument.

Cryo and RF ablation catheters create lesions of different characteristics, and in a cardiac setting, one type may be preferred for treating lesions. Thus, freezing lesions may take longer to generate, allowing the operator to terminate the ablation to avoid adverse effects, and the lesions may be of lesser extent, so that they heal more quickly. These factors may dictate choosing a cryoablation catheter when the treatment sites are located in a tin cardiac wall. For open surgery the particular limitations or benefits of one or the other catheter may be addressed by special constructions, such as providing two sided tissue contacting plates for cooling or for providing RF energy through the target tissue, however, for endovascular use each type of catheter remains subject to distinct limitations.

Cryocatheters may be adapted for endovascular insertion, or for insertion along relatively confined pathways, for example through a body lumen, or through a small incision to and around intervening organs, to reach an intended ablation site. As such, they are characterized by a relatively elongated body trough which the cooling fluid must circulate, and a tip or distal end portion where the cooling is to be applied. The requirement that the coolant be localized in its activity poses stringent constraints on a working device. For example when the catheter contact must chill tissue to below freezing, the coolant itself must attain a substantially lower temperature. Furthermore the rate of cooling is limited by the ability to supply a sufficient mass flow of coolant and to circulate it through the active contact region, and the efficacy of the contact region itself is further limited by geometry and physical properties that affect its ability to conduct heat into the tissue. The rate of cooling may change depending upon the effectiveness of thermal contact, e.g. upon the contact area and contact pressure between the catheter and the tissue, and may be further influenced by ice accumulations or other artifacts or changes due to the freezing process itself. Moreover, it is a matter of some concern that proximal, adjacent or unintended tissue sites should not be exposed to harmful cryogenic conditions. These somewhat conflicting requirements make the actual implementation of an effective cryocatheter complex. One such device treats or achieves a relatively high rate of heat transfer by providing a phase change coolant which is pumped as a liquid to the tip of the catheter and undergoes its phase change in a small chamber located at the tip. The wall of the chamber contacts adjacent tissue directly to effect the cooling or ablation treatment. By employing a phase change refrigerant injected at ambient temperature along the body of the catheter to undergo expansion at the tip, the cooling effect may be restricted to the localized treatment region surrounding the tip portion of the device. The dimensions of catheter construction, particularly for an endovascular catheter, require that the phase change coolant be released from a nozzle or tube opening at a relatively high pressure, into a relatively small distal chamber of the catheter. After the fluid vaporizes and expands in the distal chamber and cools the walls, it is returned through the body of the catheter to a coolant collection system, preferably in the form of a recirculation loop.

For such a cryocatheter, coolant is released at high pressure in a relatively small chamber at the tip of the catheter and recirculates back via a return conduit from the tip region. For cardiac ablation, the injection is controlled from a low rate of delivery for cold mapping or treatment site confirmation, to a higher rate of delivery used for tissue ablation at the mapped or confirmed sites. Thermal transfer may vary as ice accumulates on the tip. For other applications such as thermal angioplasty, proper treatment may require precise control of the cooling in other temperature ranges. Me wide range of required energy transfer rates as well as differences in size, shape or construction of different catheters increases the difficulty of achieving uniform or repeatable catheter cooling rates. This has resulted in instruments that operate in restricted temperature ranges and with wide variations in their cooling characteristics.

RF ablation catheters for ablating tissue and cardiac treatment by the localized application of RF energy are of similar size, and typically employ a catheter tip construction in which a monopolar or a bipolar (split) electrode tip applies an AC electrical signal to tissue in contact with the electrode. In this technology, cooling fluid may also be applied to prevent excessive heating of the electrode itself, or to chill tissue and allow cold-mapping during a treatment regimen. Other special constructions such as the use of an electrically conductive saline irrigant, may be used to extend the size of the lesion, and cardiac signal sensing electrodes may also be spaced along the length of the tip, allowing a single instrument to detect and map cardiac signals during treatment. However, RF catheters typically operate quite locally. Resistive tissue heating falls off with the fourth power of distance, and while electrode cooling may somewhat change their heating characteristics, their limited range of operation often necessitates lengthy treatment procedures involving many iterations of cold mapping, ablative lesion forming, and re-mapping or checking steps. The necessary number of steps may require over an hour to perform.

Accordingly, there remains a need for a catheter construction that achieves an extended range of thermal transfer.

There is also a need for a cryocatheter construction that ablates tissue more effectively, or to a greater depth.

There is also a need for a cryocatheter construction that is controllable to provide uniform and repeatable thermal treatment over a wider range of thermal energy transfer conditions.

SUMMARY OF THE INVENTION

One or more of these and other desirable features are achieved in a catheter that includes a treatment segment with both heating and cryoablation elements and a controller that operates both these sets of elements to control the extent of the ablation lesion. The catheter may, for example, be a modified phase-change cryocatheter with a tip through which a controllably injected phase change coolant circulates to lower the tip temperature, and also possessing an RF electrode assembly. The cryogenic and RF supplies are operated in coordination to set a tip environment or to condition the tissue, also applying a destructive thermal extreme in the adjacent tissue. Starting from a set tip temperature and initial time interval, which may for example condition the surrounding tissue, a controller operates one or both tip energy sources to ablate the tissue. The RF electrode may be operated to affect the depth or location of a lesions or to thaw cryogenically-cooled tissue, and/or to reduce the time or movement sequence between successive ablations. Similarly, the coolant may be controlled to chill the tissue prior to or during an RF ablation or warming treatment regimen, allowing greater versatility of operation and enhancing the speed or placement lesions in a treatment cycle. In one electrical embodiment, the electrode is configured for applying microwave energy to penetrate and undergo preferential absorption beyond an ice boundary, thus extending the depth or range of a cryoablation treatment target region. In another embodiment, the cooling and application of RF energy are controlled to balance energy flux in the near field while heating (or cooling) the far field so as to position an ablation region away from the surface contacted by the electrode. The driver or RF energy source may supply microwave energy at a level effective to prevent ice formation in the near field yet deliver a cumulatively destructive level of heating at depth, or it may be configured to apply microwave-band energy after initial freezing, at a frequency effective to penetrate the ice ball which develops on a cryocatheter, and with an absorption coefficient effective to form an ablation layer of defined thickness that either extends to, or starts at a defined distance or depth. The controller may also select a thermal set point to initiate or to carry out treatment for different tissue applications at a temperature between 70 and minus 70 degrees Celsius, so that a temporally offset thermal conduction profile is applied to an RF heating profile. For example, the cryogenic segment may be operated to pre-chill adjacent tissue before RF ablation commences, so as to permit the RF energy to be applied for a longer time without prematurely or excessively denaturing the tissue near the electrode. When operating with microwave energy through a cryogenic ice ball, the catheter may extend the depth and width of the region of active ablation, allowing a small endovascular catheter to create larger ablations in a controlled manner. The cryocatheter may be fitted with a bipolar RF ablation electrode assembly positioned to facilitate lesion placement.

BRIEF DESCRIPTION OF THE DRAWINGS

The invention will be more fully understood from the following detailed description taken in conjunction with the accompanying drawings, in which.

DETAILED DESCRIPTION

Figure 1:
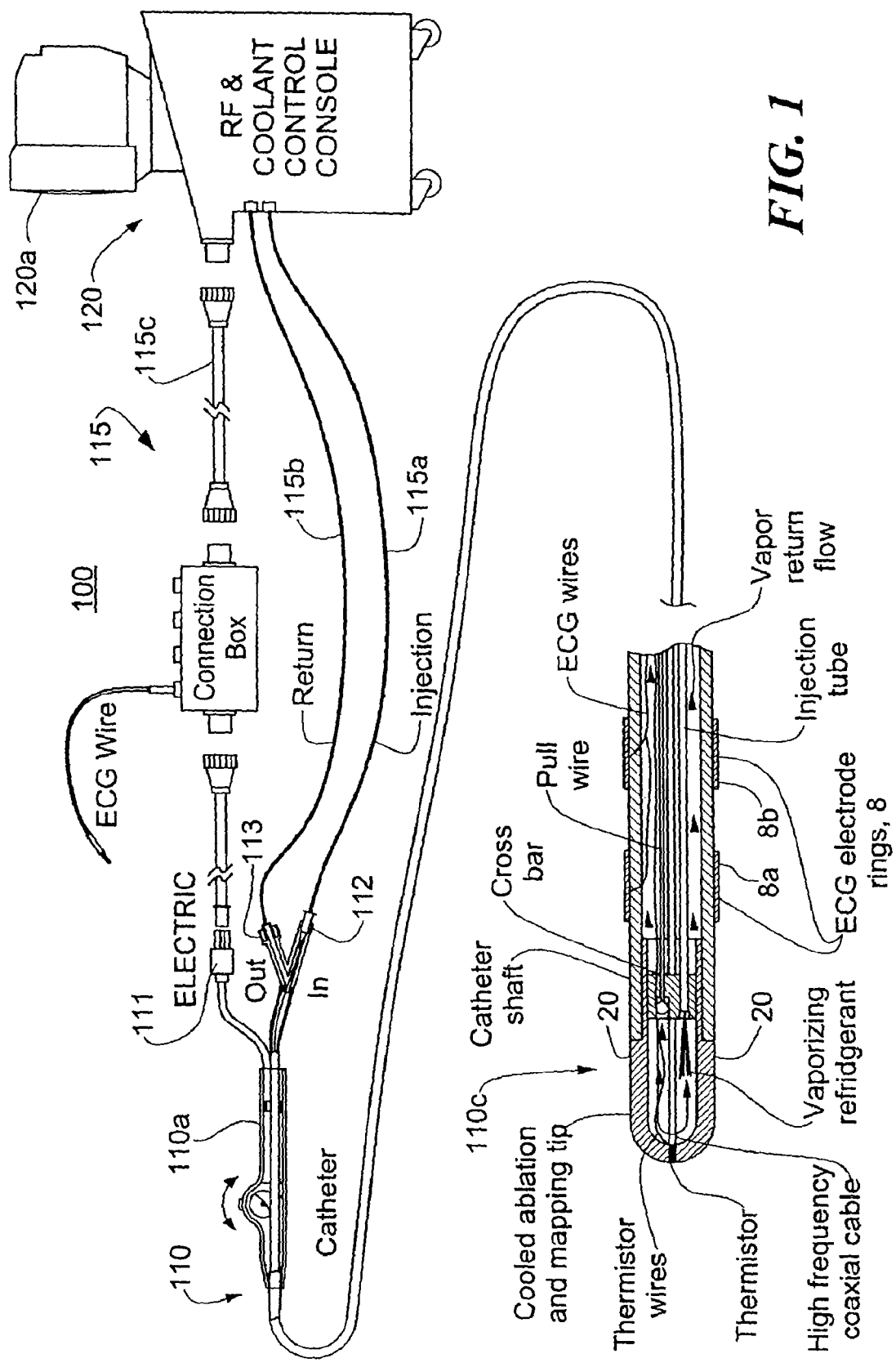
FIG. 1 shows a first embodiment of a cryoablation RF catheter and system of the present invention.

FIG. 1 shows a first embodiment of a cryogenic treatment system 100 of the present invention and illustrative elements thereof. System 100 includes a treatment catheter 110 having a handle 110a, and elongated cryogen transporting body 110b and a catheter tip 110c. The catheter 110 is connected by various conduits or cables to a console 120 which may, for example, have a display monitor 120a and other data entry or display accessories such as a keyboard, a printer and the like. The console 120 is connected to the catheter by various lines 115 which may include a coolant injection line 115a, a coolant return line 115b, and electrical cabling 115c which includes an RF drive line and may further carry console control outputs such as valve or switching signals, and outputs of various cardiac sensing, thermal sensing, mapping or other elements for catheter treatment or monitoring. As shown, the handle 110a is equipped with input ports for electrical connectors 111, a coolant injection tube connector 112, and a return tube connector 113. These are connected by various internal leads, junctions or tubes passing through the handle and elongated body 110b to the distal tip of the catheter. The handle may also include various control assemblies, e.g., switches or valves, as well a safety detection or shutdown elements (not illustrated).

As shown schematically in FIG. 1, the coolant is carried to the tip trough an injection tube 1 and enters a chamber at the end of the catheter tip 110c to expand and/or vaporize in a small contained region forming the active cooling region of the tip of the catheter. By way of example, the tube 1 may run concentrically within the elongated body 110b, and the portion of the body lumen outside of tube 1 may form a return passage for spent coolant. The tube 1 runs to the tip of the catheter where coolant exits from one or more orifices into the chamber and returns through all or a portion of the annular space surrounding tube 1, to the fluid return connector 113 of the handle. Preferably the return passage for expended coolant is a vacuum passage, thus assuring that leakage out of the catheter into the bloodstream does not occur in the case of a puncture in the catheter wall. In addition, the cooling tip also serves as an RF tip electrode 20 and connects through the catheter and handle to an RF driver, as discussed further below, for heating and ablating tissue. The tip-RF electrode 20 may be a split, or bipolar electrode, or a single conductor body.

In the illustrated embodiment, the chamber in which coolant is released from the nozzle and returns to the return passage via annular opening, defines a cooling region of the catheter tip. This chamber may be short, less than a few centimeters long, and located at the very tip of the catheter or slightly proximal thereto. A thermocouple or thermistor 5 and one or more ring electrodes 8a, 8b, . . . , (FIG. 1) are also shown in or on the catheter tip for performing thermal sensing and tissue impedance or conduction signal monitoring functions.

The foregoing description describes a catheter system in general terms with a cryogenic cooling mechanism and an RF electrode assembly as well as several sensing elements useful in such a system. Preferably in this cryoablation system a phase change coolant is injected through the injection tube 1 to vaporize and expand at the tip of the catheter, and return via a vacuum or suction passage to the return connection 113 at the catheter handle. Also the phase change material is preferably provided at ambient temperature but relatively high pressure through the handle and body 110a, 110b of the catheter, such that cooling only occurs upon release of pressure and expansion within the chamber at the tip of the catheter. Cooling operation of this device involves controlling the timing and amount of coolant injected through the injection tube 1 at the injection pressure, which may, for example, be a pressure of about 400 psig. The entire catheter may be dimensioned for endovascular deployment to fit through a No. 9 French introducer or smaller, and attain a catheter tip temperature down to about −70° C. In its cooling aspects the tip acts on surrounding tissue by thermally conductive contact. In addition, the RF heating of the tip 20 allows operation of the catheter to heat surrounding tissue with an energy profile that is different from and independent of the cooling profile of the catheter tip. The RF energy may heat tissue to temperatures of +70° C. or more, and it operates with a different mechanism and heat generation profile tan the thermal conduction profile of the cooler. The controller operates these two systems, in various treatment regimens of the invention described further below, to condition and treat tissue in the same procedure, which may for example, effect mapping or ablation; position or shape the treatment region, extend the reach of ablation treatment; or reduce the time required between steps of a multi-step ablation or combined ablation/mapping operation.

Figure 2:
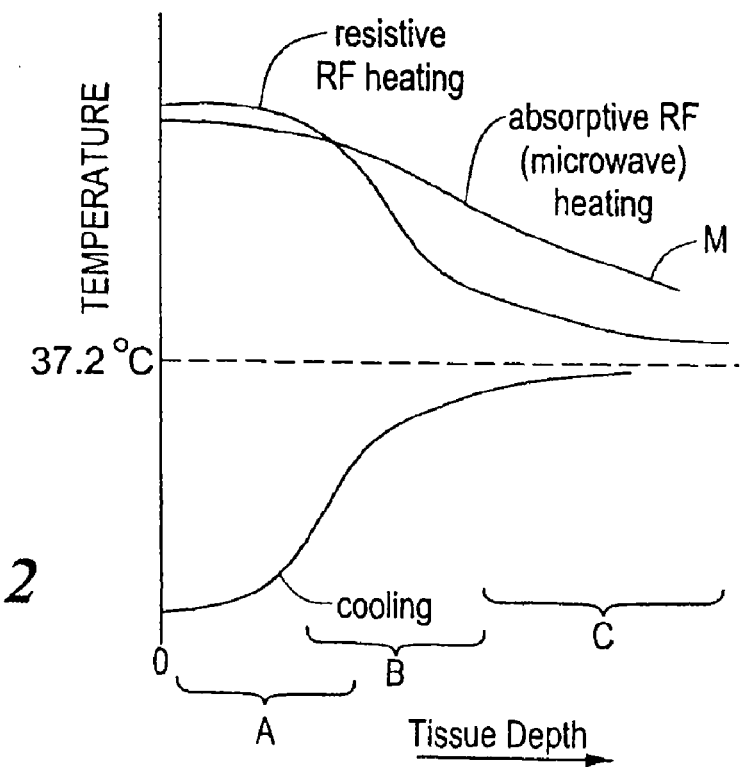
FIG. 2 shows representative RF (including microwave) and thermal conduction temperature profiles.

FIG. 2 shows, by way of example representative tissue temperature profiles, as a function of depth for various thermal systems. The horizontal axis corresponds to tissue depth from a surface at the origin, while the vertical axis corresponds to tissue temperature with body temperature at 37° C. indicated by the horizontal dashed line. No scale is given or intended, and the curves are presented to illustrate the general form of a temperature profile at a fixed instant in time after the application of treatment energy for time intervals which may differ for each energy source, but that have been found effective to provide mapping or to create an ablation lesion. By way of example, the necessary contact time for a cryocatheter may be on the order of one-half to three to minutes, and the RF energy application time for an RF ablation catheter may be on the order of tens of seconds.

As shown in FIG. 2, the thermal profile introduced into adjacent tissue by contact with a cryogenic treatment probe is a temperature that increases with depth having its lowest temperature at the contacted surface and increasing to a temperature somewhat below normal body temperature. This cryoablation curve in FIG. 2 has a relatively shallow distribution of extreme cold. The tissue depth is illustratively shown as having a first surface region A of extreme temperature followed by an intermediate depth region B of intermediate temperature and a deeper region C approaching normal temperature. By way of example each of the regions A, B may have a thickness below one centimeter and typically in the range of one to six millimeters. The precise shape of the lesion and distribution of damage regions depends upon the size, shape, thermal conductivity and cooling power of the cryogenic segment. In general, this will vary for constructions based on hypocooled saline, phase change refrigerant, Joule-Thomson or other cooling assemblies.

As further shown in FIG. 2, a typical thermal profile obtained by RF ablation stars at a temperature substantially above normal body temperature at the electrode contact surface, and remains extremely hot to a somewhat greater depth, then drops quickly with increasing depth. It will be appreciated by those skilled in the art that the term "RF" as used in this context customarily refers to an AC signal of a suitably high frequency (typically over 30-50 kHz) so as to not introduce pain or muscle contractions, but that its typical mode of propagation is that of electrical conduction and resistive heating rather than electromagnetic wave propagation and attenuative absorption more typically associated with radio waves. As such, the rate at which RF energy delivers heat to tissue depends substantially on the impedance pathways to a distant ground electrode (for a monopolar device), or between electrodes of a bipolar device. Typically, heating drops with the fourth power of distance from the electrode, but the volume distribution profile may be improved with a broad surface electrode or larger catheter electrodes in the monopolar case, or by other means. Thus the RF heating profile in FIG. 2 is intended as a representative profile but will be understood to vary, for example, with different electrode configurations, applied radio frequencies and average power levels, to influence the relative increase in heat, given the locally available heat conduction from blood circulation and other tissue-related physical parameters. In accordance with one aspect of the invention described below in regard to FIGS. 5A to 5D, the invention may include a hybrid RF cryocatheter with an exposed or projecting pair of electrodes tailored to produce a desired ablation lesion.

Finally, the third curve M in FIG. 2 illustrates a typical profile for tissue heating with microwave energy. In this circumstance the applied energy has a microwave frequency, which may be selected, for example, so that its absorption coefficient in tissue depends substantially on factors other than electrical conductivity, such as the presence or concentration of hydroxyl groups or the like in the targeted tissue. In this case the energy applied and absorbed by tissue may drop off with a lower power function, so it has a more uniform profile extending at a depth into the tissue. The curve M accordingly may achieve a deeper lesion of more uniformly applied energy. Thus, FIG. 2 illustrates three representative thermal profiles achievable by separate mechanisms of RF, microwave electrical, and cooling ablation (which, may be effected by a phase change, Joule-Thomson, liquid cooling or other thermal source.)

Figure 2A:
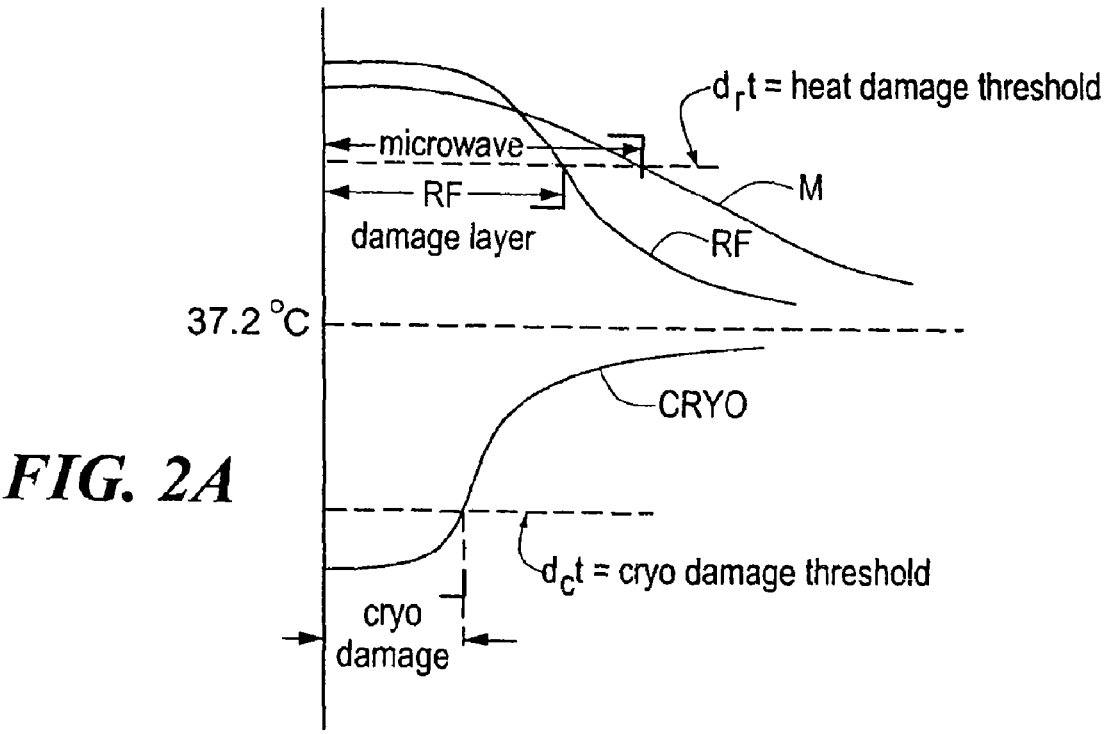
FIG. 2A illustrates thermal conduction and RF treatment regions with overlaid profiles.

By way of illustration, FIG. 2A shows the profiles of FIG. 2 overlaid on a chart showing the effective ablation lesion extent, depth or distance from the catheter tip. As illustrated in that figure for cryogenic treatment, all tissue which has attained a cooling or freezing temperature below a first damage threshold at a distance $d_c t$ below normal body temperature is ablated. All tissue which lies above a temperature elevation damage threshold minimum $d_r t$ is destroyed by heating in the RF heating or microwave cases. As shown in the figure, ablation starts at the surface in all three cases and extends to a depth which varies with the particular type energy employed.

For each of the above three treatments, the individual treatment deposits, or in the case of cooling, removes thermal energy at a characteristic rate which, in combination with the thermal conduction of surrounding tissue, results in a buildup of the local temperature difference that is effective to ablate tissue. Each mode of heating or cooling requires time to introduce this temperature change, and each acts against the ongoing thermal conduction by surrounding tissue which effectively limits the extent of the resulting lesion. In accordance with a principal aspect of the present invention, a controller applies cryogenic cooling in conjunction wig one or more of the electrically-driven, e.g., RF and microwave, energy sources to overlay heating and cooling profiles with the tip temperature selectable between an extreme cold and an extreme hot range. The two modes are synchronized to affect the shape of the ablated tissue region, to reduce time for successive mapping/ablation steps, or to achieve a targeted ablation. The respective heating and cooling mechanisms may be configured such that their opposed effects are in equilibrium with normal conductive cooling by the surrounding tissue at a defined depth, thus forming a self-limiting lesion of defined size.

To simplify the discussion herein, the term "RF ablation catheter" or the descriptor "RF," shall be used here and in the following claims to include microwave catheters and microwave signals in addition to the high frequency AC and radio frequency catheters and drive signals customarily denoted by those terms. It will be understood, however, that microwave catheters and microwave control consoles will have a distinct construction from devices employed at lower (on-microwave rf) frequencies, and the construction of hybrid cryo/microwave devices, while not specifically illustrated, will be understood to generally involve the incorporation of cryogenic cooling and control elements in a microwave device, with appropriate care to avoid adverse interactions of the two structures, such as microwave absorption by the coolant or antenna resonance effects of the metal components.

Figure 3:
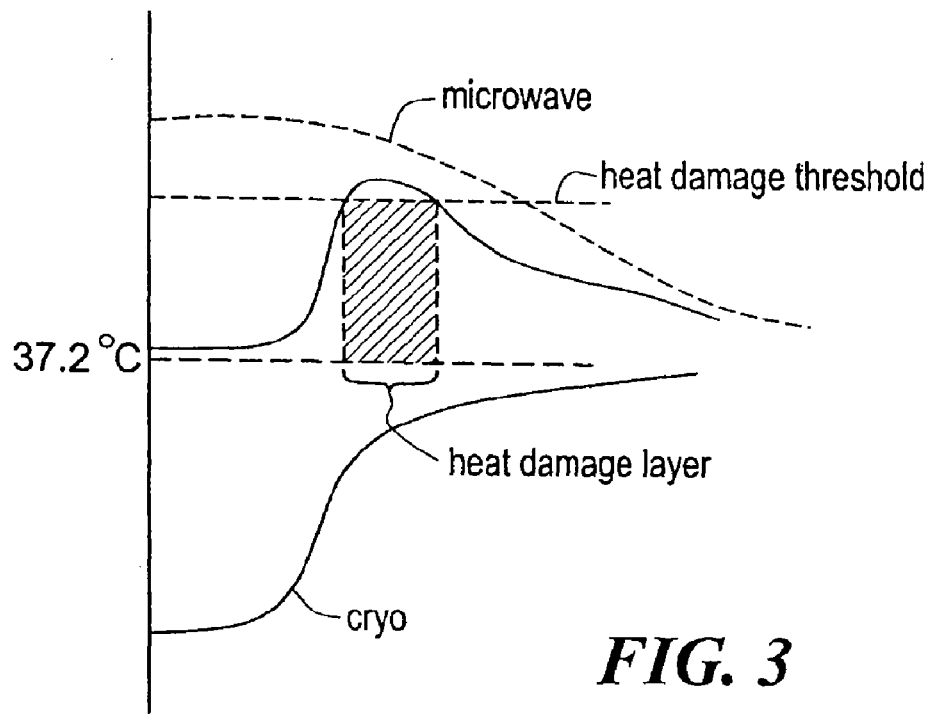
FIG. 3 shows a combined ablation of the invention.
Figure 4:
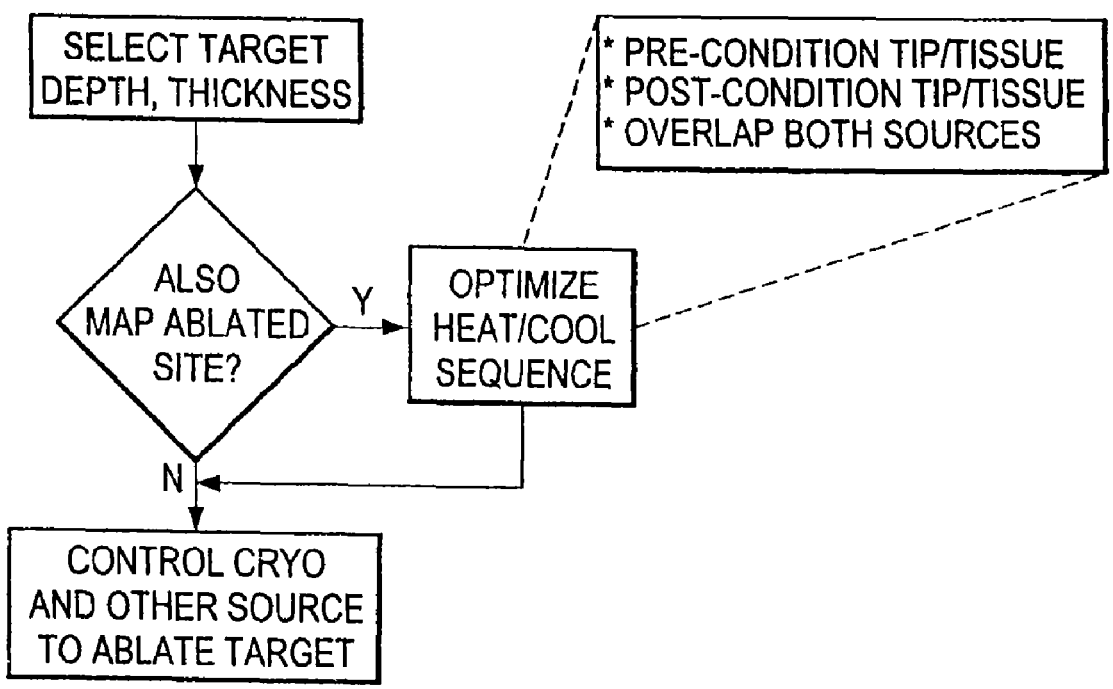
FIG. 4 shows one operating method of the control console.

Continuing with a description of the operation of applicant's ablation procedures wherein the controller operates the two different types of ablation elements in a hybrid catheter, FIG. 3 illustrates one such thermal profile of the present invention formed by overlaying a profile such as the cryotreatment curve of FIG. 2 plotted as a dashed line below the nominal body temperature, and an RF profile such as the microwave curve M of FIG. 2 plotted as a dashed line above normal temperature. As shown, the heating and cooling induced respectively by cryogenic thermal conduction and by the application of electromagnetic energy counterbalance each other in the near field so that the thermal profile remains always well within the damage threshold and no ablation occurs throughout the surface region A of tissue depth. In the intermediate depth region B where the magnitude of the cooling effect is smaller, the heating dominates, and tissue temperature rises above the damage threshold to produce ablation in a limited range or layer L of tissue located remotely from the catheter contact surface. By operating the microwave source at higher power or for a longer time while still cooling the surface by thermal contact, the thickness or depth of layer L may be increased while the surface remains below the heat damage threshold. Alternatively the cryocoolant may be applied first to ablate a surface lesion, and the RF or microwave electrode activated second to restore normal surface temperature while initiating a depth lesion. In this case the hybrid catheter may have a cryo/microwave structure, and the controller may also operate sensing or mapping electrodes to verify the efficiency of the surface treatment during the continued ablation at depth. In this type of treatment, the controller may select different frequencies of microwave power to achieve the correct heating power distribution, to penetrate the ice ball that would otherwise stymie a resistive heating approach, or to otherwise tailor the application of energy to ablate the specified target tissue.

As shown in FIG. 3, the simple overlaying of two thermal treatment profiles may result in control of tissue damage locally and placement of a lesion at a normally inaccessible depth. It will also be understood that in practice the two treatment modes may interact with each other, so that, for example, cryogenic cooling reduces circulation and thus increases the rate at which an RF signal would otherwise heat up tissue, with the result that simultaneous application of the two normally different ablation regimens does not have the effect indicated by simple addition of the two thermal profile curves.

In general, the microwave treatment, being able to penetrate through the near tissue and effect heating at a depth before any cooling action has propagated by thermal conduction, may define a remote lesion without damaged surface tissue. When applying a lower frequency RF heating signal rather than microwave treatment, the cooling and heating effects may be rendered more independent of each other by applying them at offset time intervals so that, for example the near tissue is lowered in temperature prior to commencing RF heating. This has the effect of shifting the RF damage curve downwardly from the surface, or eliminating it in the near field. The RF energy, if applied for a longer time interval, may produce a lesion at depth, without damage to the surface tissue. The amount of applied surface cooling may be reduced, or terminated and the RF energy may also be applied for an even longer period to achieve the usual degree of ablation at the surface, but with tissue damage extending more deeply than is achieved with a pure RF ablation.

In another method of control, by operating the catheter to precondition or concurrently counteract the temperature of the tissue heated by RF, cold mapping may be carried out while the RF energy is being applied to tissue, thus simultaneously confirming a target site and reducing the sequential time intervals formerly required for mapping and ablation procedures.

The catheter may also be used to create cryogenic lesions, and, in other treatment regimens, the RF or microwave electrode is operated to preheat tissue, raise the tip temperature, or to warm tissue after cryoablation to allow signal mapping to be undertaken immediately. One particularly advantageous embodiment of this aspect of the invention employs a catheter which is operated as a drag line to lay down a linear lesion so that cooling and RF energy are both applied continuously as the tip is moved along the surface, for example, of an endocardial wall. The elongated chamber of the cardiac tip may operate with a relatively slow time constant to chill tissue along the intended path while mapping ahead of the RF electrode, and this electrode may then be actuated with a shorter time interval and/or higher power level to place lesions at an appropriate position in the endocardial wall, as determined by the previous mapping. Such operation is believed to be particularly advantageous for operations such as creating conduction blocks in complex cardiac pathways where deep or even external tissue (i.e. the exocardial wall surface) may be sustaining a reentrant arrhythmia.

One method of using the cooled RF ablation catheter is to carry out conventional cold mapping, followed by the controlled hybrid ablation. While both the cooling system and the RF system are off, the physician introduces the catheter through an artery (a femoral artery, the carotid or other main artery) to a chamber in the heart where a suspected pathology is present. The physician radiographically observes the tip during the progression of the catheter distal end into the heart, to position it against the inner wall of the heart. The physician then moves the catheter to be in thermal contact with a suspected pathological site within the heart, and then turns on the cooling system to reduce the temperature of the catheter tip. During the whole process, the heart electrical activity may be monitored, either with catheter electrodes, or with external EKG electrodes. Cooling of the site responsible for the arrhythmia or other electrical abnormality stops the abnormal electrical activity, thus confirming that the correct site has been selected. If cooling does not stop the abnormal activity, the physician then moves the catheter tip to another suspected site util he has found the arrhythmogenic locus. Once this site has been selected, the cooling and the RF power are controlled to create the desired lesion. This may be a cryogenic lesion, created by further reducing the tip temperature, an RF lesion formed with a controlled tip temperature, or other controlled lesion as discussed above. The two sources may also be operated to warm or cool the site, as appropriate, in order to restore normal tissue temperature and monitor electrical activity for confirming the efficacy of treatment. Freezing/heating cycles may also be alternated to more effectively destroy tissue in the ablation site.

It will be appreciated that the above-described system provides a new and useful tool for ablation treatment, and that in use, handling and operation of the device will immediately suggest further variations and methods of operation to the skilled user. Thus, for example, by observing the response of cardiac signals to cooling as the catheter is advanced to a site, the user may estimate the depth, extent, or proximity of a targeted triggering lesion or signal pathway, and may select an appropriate ablation cycle of the heating and cooling elements to most effectively ablate the particular target. One skilled in the art will appreciate further features and advantages of the invention based on the above-described embodiments, and, having described the invention, further variations and modifications within the spirit and scope of the invention will occur to those skilled in the art. Accordingly, the invention is not to be limited by what has been particularly shown and described, but is understood to be defined by the claims appended hereto and their equivalents.

The invention claimed is:

1. A catheter for the treatment of tissue having a controller, comprising:
    a catheter body,
    a treatment tip positioned on the catheter body, the tip having a cryogenic cooling segment for contacting and thermally treating tissue, and an electrically-driven ablation assembly, the electrically-driven ablation assembly operable by the controller to apply heating ablation energy to the tissue and ablate the tissue simultaneously with the cooling segment.

2. The catheter of claim 1, wherein the cooling segment operates to ablate the contacted tissue to a predetermined cooled tissue boundary and the electrically-driven ablation assembly operates to extend ablation beyond the predetermined cooled tissue boundary.

3. The catheter of claim 1, wherein the tip further comprises one or more sensing electrodes, the sensing electrodes usable to cold-map cardiac tissue sites.

4. The catheter of claim 1, wherein the electrically driven ablation assembly and the cooling segment are arranged to provide a predetermined tip temperature.

5. The catheter of claim 1, wherein the cooling segment is coolable to about $-70°$ C.

6. The catheter of claim 1, wherein the electrically-driven ablation assembly includes an electrode assembly for applying radio frequency energy.

7. The catheter of claim 6, further comprising a driver providing the radio frequency energy at a frequency effective to achieve enhanced absorption in the thermally treated tissue at a depth beyond a thermal conduction depth of the cooling segment.

8. The catheter of claim 1, wherein the electrically-driven ablation assembly and the cooling segment operate to prevent near field charring during ablation.

9. The catheter of claim 1, wherein the electrically-driven ablation assembly and the cooling segment operate to prevent near field icing during ablation.

10. The catheter of claim 1, wherein the electrically-driven ablation assembly and the cooling segment operate to maintain a non-ablating near field temperature while attaining an ablation temperature at a depth beyond a thermal conduction depth of the cooling segment.

11. A catheter for the treatment of tissue, comprising:
    a catheter body,
    a treatment tip positioned on the catheter body, the tip having a cryogenic cooling segment for contacting and thermally treating tissue, and an electrically-driven ablation assembly, the electrically-driven ablation assembly operable to apply heating ablation energy to the tissue, the cooling segment ablates contacted tissue to a predetermined cooled tissue boundary and the electrically-driven ablation assembly extends ablation beyond the predetermined cooled tissue boundary.

12. The catheter of claim 11, wherein the tip further comprises one or more sensing electrodes, the sensing electrodes usable to cold-map cardiac tissue sites.

13. The catheter of claim 11, wherein the electrically driven ablation assembly and the cooling segment operate simultaneously to provide a predetermined tip temperature.

14. The catheter of claim 11, wherein the cooling segment is coolable to about $-70°$ C.

15. The catheter of claim 11, wherein the electrically-driven ablation assembly includes an electrode assembly for applying radio frequency energy.

16. The catheter of claim 15, further comprising a driver providing the radio frequency energy at a frequency effective to achieve enhanced absorption in the thermally treated tissue at a depth beyond a thermal conduction depth of the cooling segment.

17. The catheter of claim 11, wherein the electrically-driven ablation assembly and the cooling segment operate to prevent near field charring during ablation.

18. The catheter of claim 11, wherein the electrically-driven ablation assembly and the cooling segment operate to prevent near field icing during ablation.

19. The catheter of claim 11, wherein the electrically-driven ablation assembly and the cooling segment operate to maintain a non-ablating near field temperature while attaining an ablation temperature at a depth beyond a thermal conduction depth of the cooling segment.

* * * * *